United States Patent [19]
Galivan et al.

[11] Patent Number: 5,962,235
[45] Date of Patent: Oct. 5, 1999

[54] HUMAN AND RAT GAMMA GLUTAMYL HYDROLASE ANTIBODIES

[75] Inventors: John Henry Galivan, Albany; Thomas John Ryan, Schenectady; Rong Yao, Albany; Zenia Nimec, Watervliet, all of N.Y.

[73] Assignee: Health Research, Incorporated, Albany, N.Y.

[21] Appl. No.: 09/128,722

[22] Filed: Aug. 4, 1998

Related U.S. Application Data

[62] Division of application No. 08/628,291, Apr. 5, 1996, Pat. No. 5,801,031.

[51] Int. Cl.$^6$ .......................... G01N 33/53; A61K 39/395
[52] U.S. Cl. .................... 435/7.1; 530/387.1; 530/388.1; 530/388.15; 530/388.26; 530/389.1
[58] Field of Search .......................... 435/7.1; 530/387.1, 530/388.1, 388.15, 388.26, 389.1

[56] References Cited

FOREIGN PATENT DOCUMENTS

WO 95/14772  1/1995  WIPO .

OTHER PUBLICATIONS

Israeli, R.S., et al., Cancer Research 53:227–230 (1993).
Pinto, J.T., et al., Clinical Cancer Research 2(9):145–1451 (1996).
Leek, J., et al., Br J Cancer 72(3):583–588 (1995).
Silver, D.A., et al., Clinical Cancer Research 3:81–85 (1997).
Chandler et al., Am J Physiol 260:G865–G872 (1991).
Wang et al., Biochim Biophys Acta 1164:227–235 (1993).
McGuire, J.J. and Coward, J.K., in "Folates and Pterins: Vol. 1 Chemistry and Biochemistry of Folates", Blakely, R.L. and Benkovic, eds., John Wiley & Sons, Inc., New York, pp. 135–190 (1984).
Acc. #T26504, n–gene seq. database.
Acc. # N45706, R77701, N53343, H09442, and N48195, EST database (Hillier et al.).
Tao et al. J. Biol. Chem. 271:8525–8528, Apr. 12, 1996.

*Primary Examiner*—John L. LeGuyader
*Attorney, Agent, or Firm*—Braman & Rogalskyj, LLP

[57] ABSTRACT

The present invention is directed to isolated nucleic acid molecules encoding gamma glutamyl hydrolase (GH). Expression vectors and host cells comprising the nucleic acid molecules are also provided, as well as methods for increasing or decreasing the expression of GH in host cells. The invention further provides a method of screening a substance for the ability of the substance to modify GH function, and a method for isolating other GH molecules. DNA oligomers and antibodies specific for GH are provided, each of which can be used to detect GH in a sample. Methods for decreasing deleterious side effects of antifolate treatment, increasing the levels of GH in cells of a patient, increasing the effectiveness of antifolate treatment, and monitoring progression of a tumor are further provided.

6 Claims, No Drawings

HUMAN AND RAT GAMMA GLUTAMYL HYDROLASE ANTIBODIES

This application is a divisional of U.S. Ser. No. 08/628,291, filed Apr. 5, 1996 now U.S. Pat. No. 5,801,031.

The subject matter of this application was made with support from the United States Government under grant CA 25933 of the National Cancer Institute, National Institutes of Health.

FIELD OF THE INVENTION

The present invention relates generally to the peptidase gamma glutamyl hydrolase, and more particularly to nucleic acid molecules encoding gamma glutamyl hydrolase and uses thereof.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

Gamma glutamyl hydrolase (GH) (EC 3.4.22.12) catalyzes the hydrolysis of the polyglutamate side-chain folyl polyglutamates and antifolyl polyglutamates (Stokstad and Koch 1967; Elsenhans et al. 1984; Chandler et al. 1986; Silink et al. 1975; Horne et al. 1981; Samuels et al. 1986; Bhandari et al. 1990; Rosenberg and Neuman 1974; Priest et al. 1982; Saini and Rosenberg 1974; Shin et al. 1974; McGuire and Coward 1984; Wang et al. 1986; Rao and Noronha 1977; Reisenauer et al. 1977; Wang et al. 1993). Gamma glutamyl hydrolase has been characterized from a number of sources, and it exhibits either endo- or exopeptidase activity, depending upon the tissue of origin (Stokstad and Koch 1967; Elsenhans et al. 1984; Silink et al. 1975; Horne et al. 1981; Samuels et al. 1986; Bhandari et al. 1990; Rosenberg and Neuman 1974; Priest et al. 1982; Saini and Rosenberg 1974; Shin et al. 1974). In many tissues the enzyme is lysosomal with an acidic pH optimum (McGuire and Coward 1984). In addition, the enzyme is often sulfhydryl- and $Zn^{2+}$-dependent (Chandler et al. 1986; Silink et al. 1975; Horne et al. 1981; Bhandari et al. 1990; McGuire and Coward 1984; Wang et al. 1986; Rao and Noronha 1977; Wang et al. 1993), appears to be a glycoprotein in many cases (Silink et al. 1975; Wang et al. 1993), and has a reported molecular weight of 50 to 150 kDa (Elsenhans et al. 1984; Chandler et al. 1986; Silink et al. 1975; Priest et al. 1982; McGuire and Coward 1984; Rao and Noronha 1977; Reisenauer et al. 1977; Wang et al. 1993). A thorough analysis of the mechanism of this unique peptidase that cleaves only gamma glutamyl linkages is not available and a knowledge of the detailed structure of the protein and the gene encoding it are not yet delineated.

It has been shown that resistance to the antifolate 5,10-didiazatetrahydrofolate can be acquired by enhancement of GH enzyme activity in rat H35 hepatoma cells (Rhee et al. 1993). In addition, GH is hormonally controlled, with both insulin and estrogen altering its activity in responsive cell lines and tissues (Wang et al. 1993; Galivan and Rhee 1995; Krumdieck et al. 1975). For many years it was thought that GH was a lysosomal enzyme, but recent studies using cell culture systems have shown that while its intracellular location is primarily the lysosome, most of the enzyme activity is secreted, a feature that appears thus far to be universal in neoplastic cells (O'Connor et al. 1991; Yao et al. 1995; Rhee et al. 1995).

The availability of the cDNA and amino acid sequence for GH and a polyclonal antibody to the protein offers the possibility of investigating a number of questions concerning this enzyme. The role of GH in the cellular metabolism of folylpolyglutamate coenzymes and in the cytotoxic activity of antifolates can be evaluated in detail. GH activity is known to be altered by a number of factors including insulin (Galivan and Rhee 1995), estrogen (Krumdieck et al. 1975), and selection for resistance with 5,10-didiazatetrahydrofolate in rat (Rhee et al. 1993; Yao et al. 1995) and human (Pizzorno et al. 1995) cell lines. With the availability of molecular and immunological probes, the mechanism of alterations in GH activity can be investigated. The cellular trafficking of the glycoprotein can be approached with an emphasis on the mechanism and significance of secretion. These probes could be used to evaluate the abundant secretion of GH by human breast cancer cell lines in culture (Rhee et al. 1995), which is potentially related to the high levels of GH in serum of metastatic breast cancer patients (Baggott et al. 1987). In addition, relatively large amounts of enzyme could become available for the first time when an appropriate expression system is established, and this will allow detailed analysis of the structure and mechanism of GH.

A need continues to exist, therefore, for the determination of the nucleotide and amino acid sequences of gamma glutamyl hydrolase.

SUMMARY OF INVENTION

To this end, the subject invention provides an isolated nucleic acid molecule encoding a gamma glutamyl hydrolase. In one embodiment, the nucleic acid molecule encodes a human gamma glutamyl hydrolase, and in another embodiment the nucleic acid molecule encodes a rat gamma glutamyl hydrolase. The invention also provides an antisense nucleic acid molecule complementary to at least a portion of the mRNA encoding the gamma glutamyl hydrolase.

The isolated nucleic acid molecules of the invention can be inserted into suitable expression vectors and/or host cells. Expression of the nucleic acid molecules encoding the gamma glutamyl hydrolase results in production of gamma glutamyl hydrolase in a host cell. Expression of the antisense nucleic acid molecules in a host cell results in decreased expression of the gamma glutamyl hydrolase.

The invention further provides a ribozyme having a recognition sequence complementary to a portion of mRNA encoding a gamma glutamyl hydrolase. The ribozyme can be introduced into a cell to also achieve decreased expression of gamma glutamyl hydrolase in the cell.

The invention further provides a method of screening a substance for the ability of the substance to modify gamma glutamyl hydrolase function, and a method of obtaining DNA encoding a gamma glutamyl hydrolase.

Further provided is an isolated nucleic acid molecule encoding a gamma glutamyl hydrolase, wherein the nucleic acid molecule encodes a first amino acid sequence having at least 90% amino acid identity to a second amino acid sequence. The second amino acid sequence is, in two preferred embodiments, SEQ ID NO:2 or SEQ ID NO:4.

The invention further provides a DNA oligomer capable of hybridizing to a nucleic acid molecule encoding a gamma glutamyl hydrolase. The DNA oligomer can be used in a method of detecting presence of a gamma glutamyl hydrolase in a sample, which method is also provided by the subject invention. The invention also provides an antibody or fragment thereof specific for the gamma glutamyl hydrolase encoded by the nucleic acid molecule of the subject invention. The antibody or fragment thereof can also be used in a method of detecting the presence of a gamma glutamyl hydrolase in a sample, which method is also provided by the subject invention.

Other methods provided by the subject invention include methods of decreasing deleterious side effects of antifolate treatment, and methods of increasing the effectiveness of antifolate treatment.

DETAILED DESCRIPTION

As used herein, the term "isolated" when used in conjunction with a nucleic acid molecule refers to: 1) a nucleic acid molecule which has been separated from an organism in a substantially purified form (i.e. substantially free of other substances originating from that organism), or 2) a nucleic acid molecule having the same nucleotide sequence but not necessarily separated from the organism (i.e. synthesized nucleic acid molecules).

As further used herein, the terms "corresponding to" or "having" or "as shown in" or "consisting of" when used in conjunction with a SEQ ID NO for a nucleotide sequence refer to a nucleotide sequence which is substantially the same nucleotide sequence, or derivatives thereof (such as deletion and hybrid variants thereof, splice variants thereof, etc.). Nucleotide additions, deletions, and/or substitutions, such as those which do not affect the translation of the DNA molecule, are within the scope of a nucleotide sequence corresponding to or having or as shown in or consisting of a particular nucleotide sequence (i.e. the amino acid sequence encoded thereby remains the same). Such additions, deletions, and/or substitutions can be, for example, the result of point mutations made according to methods known to those skilled in the art. It is also possible to substitute a nucleotide which alters the amino acid sequence encoded thereby, where the amino acid substituted is a conservative substitution or where amino acid homology is conserved. It is also possible to have minor nucleotide additions, deletions, and/or substitutions which do not alter the function of the resulting gamma glutamyl hydrolase. These are also within the scope of a nucleotide sequence corresponding to or having or as shown in or consisting of a particular nucleotide sequence.

Similarly, the term "corresponding to" or "having" or "as shown in" or "consisting of" when used in conjunction with a SEQ ID NO for an amino acid sequence refers to an amino acid sequence which is substantially the same amino acid sequence or derivatives thereof. Amino acid additions, deletions, and/or substitutions which do not negate the ability of the resulting protein to form a functional gamma glutamyl hydrolase are within the scope of an amino acid sequence corresponding to or having or as shown in or consisting of a particular amino acid sequence. Such additions, deletions, and/or substitutions can be, for example, the result of point mutations in the DNA encoding the amino acid sequence, such point mutations made according to methods known to those skilled in the art. Substitutions may be conservative substitutions of amino acids. Two amino acid residues are conservative substitutions of one another, for example, where the two residues are of the same type. In this regard, proline, alanine, glycine, serine, and threonine, all of which are neutral, weakly hydrophobic residues, are of the same type. Glutamine, glutamic acid, asparagine, and aspartic acid, all of which are acidic, hydrophilic residues, are of the same type. Another type of residue is the basic, hydrophilic amino acid residue, which includes histidine, lysine, and arginine. Leucine, isoleucine, valine, and methionine, all of which are hydrophobic, aliphatic amino acid residues, form yet another type of residue. Yet another type of residue consists of phenylalanine, tyrosine, and tryptophan, all of which are hydrophobic, aromatic residues. Further descriptions of the concept of conservative substitutions are given by French and Robson 1983, Taylor 1986, and Bordo and Argos 1991.

As further used herein, the term "corresponding to" or "having" or "as shown in" or "consisting of" when used in conjunction with a SEQ ID NO for a nucleotide or amino acid sequence is intended to cover linear or cyclic versions of the recited sequence (cyclic referring to entirely cyclic versions or versions in which only a portion of the molecule is cyclic, including, for example, a single amino acid cyclic upon itself), and is intended to cover derivative or modified nucleotide or amino acids within the recited sequence. For example, those skilled in the art will readily understand than an adenine nucleotide could be replaced with a methyladenine, or a cytosine nucleotide could be replaced with a methylcytosine, if a methyl side chain is desirable. Nucleotide sequences having a given SEQ ID NO are intended to encompass nucleotide sequences containing these and like derivative or modified nucleotides, as well as cyclic variations. As a further example, those skilled in the art will readily understand that an asparagine residue could be replaced with an ethylasparagine if an ethyl side chain is desired, a lysine residue could be replaced with a hydroxylysine if an OH side chain is desired, or a valine residue could be replaced with a methylvaline if a methyl side chain is desired. Amino acid sequences having a given SEQ ID NO are intended to encompass amino acid sequences containing these and like derivative or modified amino acids, as well as cyclic variations. Cyclic, as used herein, also refers to cyclic versions of the derivative or modified nucleotides and amino acids.

As further used herein, "antifolate" refers to antifolates which are converted to polyglutamates (specifically, antifolylpolyglutamates) in host or tumor tissues. Examples of antifolates as used herein include, for example, methotrexate, aminopterin, and more recently developed antifolates such as edetrexate, lomotrexol, BW1843U89, and ZD1694 (Fleming and Schilsky 1992; Bertino 1993). The resulting antifolylpolyglutamates are then degraded by the gamma glutamyl hydrolase of the subject invention, back to the parent compound (the antifolate) and glutamic acid. In general, the antifolylpolyglutamates are more toxic due to their greater cellular retention and tighter binding to a drug target than the antifolates.

With these definitions in mind, the subject invention provides an isolated nucleic acid molecule encoding a gamma glutamyl hydrolase (GH). The nucleic acid molecule can be deoxyribonucleic acid (DNA) or ribonucleic acid (RNA, including messenger RNA or mRNA), genomic or recombinant, biologically isolated or synthetic.

The DNA molecule can be a cDNA molecule, which is a DNA copy of a messenger RNA (mRNA) encoding the GH.

In one embodiment, the GH is a human gamma glutamyl hydrolase. An example of such a human gamma glutamyl hydrolase is the GH encoded by the nucleotide sequence as shown in SEQ ID NO:1. The amino acid sequence encoded by this nucleotide sequence is shown in SEQ ID NO:2.

In another embodiment, the GH is a rat gamma glutamyl hydrolase. An example of such a rat gamma glutamyl hydrolase is the GH encoded by the nucleotide sequence as shown in SEQ ID NO:3. The amino acid sequence encoded by this nucleotide sequence is shown in SEQ ID NO:4.

The invention also provides an antisense nucleic acid molecule that is complementary to at least a portion of the mRNA encoding the GH. Antisense nucleic acid molecules can be RNA or single-stranded DNA, and can be complementary to the entire mRNA molecule encoding the GH (i.e. of the same nucleotide length as the entire molecule). It may be desirable, however, to work with a shorter molecule. In this instance, the antisense molecule can be complementary to a portion of the entire mRNA molecule encoding the GH. These shorter antisense molecules are capable of hybridizing to the mRNA encoding the entire molecule, and preferably consist of at least twenty nucleotides. These antisense molecules can be used to reduce levels of GH, by introducing into cells an RNA or single-stranded DNA molecule that is complementary to at least a portion of the mRNA of the GH (i.e. by introducing an antisense molecule). The antisense molecule can base-pair with the mRNA of the GH, preventing translation of the mRNA into protein. Thus, an antisense molecule to the GH can prevent translation of mRNA encoding the GH into a functional GH protein.

More particularly, an antisense molecule complementary to at least a portion of mRNA encoding a GH can be used to decrease expression of a functional GH. A cell with a first level of expression of a functional GH is selected, and then the antisense molecule is introduced into the cell. The antisense molecule blocks expression of functional GH, resulting in a second level of expression of a functional GH in the cell. The second level is less than the initial first level.

Antisense molecules can be introduced into cells by any suitable means. Suitable cells include tumor cells which are the target of antifolate treatment (in these cells, increased levels of the more toxic antifolylpolyglutamates are desirable, which can result from decreased hydrolysis of the antifolylpolyglutamates by GH). In one embodiment, the antisense RNA molecule is injected directly into the cellular cytoplasm, where the RNA interferes with translation. A vector may also be used for introduction of the antisense molecule into a cell. Such vectors include various plasmid and viral vectors. For a general discussion of antisense molecules and their use, see Han et al. 1991 and Rossi 1995.

The invention further provides a special category of antisense RNA molecules, known as ribozymes, having recognition sequences complementary to specific regions of the mRNA encoding the GH. Ribozymes not only complex with target sequences via complementary antisense sequences but also catalyze the hydrolysis, or cleavage, of the template mRNA molecule. Examples, which are not intended to be limiting, of suitable regions of the mRNA template to be targeted by ribozymes are any of the homologous regions identified by comparing the human and rat sequences provided herein.

Expression of a ribozyme in a cell can inhibit gene expression (such as the expression of a GH). More particularly, a ribozyme having a recognition sequence complementary to a region of a mRNA encoding a GH can be used to decrease expression of GH. A cell with a first level of expression of GH is selected, and then the ribozyme is introduced into the cell. The ribozyme in the cell decreases expression of GH in the cell, because mRNA encoding the GH is cleaved and cannot be translated.

Ribozymes can be introduced into cells by any suitable means. Suitable cells include tumor cells which are the target of antifolate treatment (in these cells, increased levels of the more toxic antifolylpolyglutamates are desirable, which can result from decreased hydrolysis of the antifolylpolyglutamates by GH). In one embodiment, the ribozyme is injected directly into the cellular cytoplasm, where the ribozyme cleaves the mRNA and thereby interferes with translation. A vector may be used for introduction of the ribozyme into a cell. Such vectors include various plasmid and viral vectors (note that the DNA encoding the ribozyme does not need to be "incorporated" into the genome of the host cell; it could be expressed in a host cell infected by a viral vector, with the vector expressing the ribozyme, for instance). For a general discussion of ribozymes and their use, see Sarver et al. 1990, Chrisey et al. 1991, Rossi et al. 1992, and Christoffersen et al. 1995.

The nucleic acid molecules of the subject invention can be expressed in suitable host cells using conventional techniques. Any suitable host and/or vector system can be used to express the GH. For in vitro expression, bacterial hosts (for example, *Escherichia coli*) and mammalian hosts (for example, Hela cells, Cv-1 cells, COS cells) are preferred. For in vivo expression, the most suitable host cell depends on the goal of the expression. For example, since antifolylpolyglutamates are toxic to bone marrow cells, it is desirable to increase expression of GH in these host cells so that the GH hydrolyzes the antifolylpolyglutamates and therefore decreases their deleterious effects on the bone marrow cells. In tumor host cells, however, where the hydrolysis effect of GH on antifolylpolyglutamates decreases the efficiency of the antifolate treatment, it is desirable to decrease or prevent expression of GH. Thus, tumor cells are a particularly suitable host in which to decrease GH expression (such as by use of antisense molecules or ribozymes, or through the use of substances which block the expression and/or action of GH).

Techniques for introducing the nucleic acid molecules into the host cells may involve the use of expression vectors which comprise the nucleic acid molecules. These expression vectors (such as plasmids and viruses; viruses including bacteriophage) can then be used to introduce the nucleic acid molecules into suitable host cells. For example, DNA encoding the GH can be injected into the nucleus of a host cell or transformed into the host cell using a suitable vector, or mRNA encoding the GH can be injected directly into the host cell, in order to obtain expression of GH in the host cell.

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA). DNA can also be incorporated into artificial lipid vesicles, liposomes, which fuse with the cell membrane, delivering their contents directly into the cytoplasm. In an even more direct approach, used primarily with plant cells and tissues, DNA is absorbed to the surface of tungsten microprojectiles and fired into cells with a device resembling a shotgun.

Several of these methods, microinjection, electroporation, and liposome fusion, have been adapted to introduce proteins into cells. For review, see Mannino and Gould-Fogerite 1988, Shigekawa and Dower 1988, Capecchi 1980, and Klein et al. 1987.

Further methods for introducing nucleic acid molecules into cells involve the use of viral vectors. Since viral growth depends on the ability to get the viral genome into cells, viruses have devised clever and efficient methods for doing it. One such virus widely used for protein production is an insect virus, baculovirus. Baculovirus attracted the attention of researchers because during infection, it produces one of its structural proteins (the coat protein) to spectacular levels. If a foreign gene were to be substituted for this viral gene, it too ought to be produced at high level. Baculovirus, like vaccinia, is very large, and therefore foreign genes must be placed in the viral genome by recombination. To express a foreign gene in baculovirus, the gene of interest is cloned in place of the viral coat protein gene in a plasmid carrying a small portion of the viral genome. The recombinant plasmid is cotransfected into insect cells with wild-type baculovirus DNA. At a low frequency, the plasmid and viral DNAs recombine through homologous sequences, resulting in the insertion of the foreign gene into the viral genome. Virus plaques develop, and the plaques containing recombinant virus look different because they lack the coat protein. The plaques with recombinant virus are picked and expanded. This virus stock is then used to infect a fresh culture of insect cells, resulting in high expression of the foreign protein. For a review of baculovirus vectors, see Miller (1989). Various viral vectors have also been used to transform mammalian cells, such as bacteriophage, vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

Host cells into which the nucleic acid encoding the GH has been introduced can be used to produce (i.e. to functionally express) the GH. The function of the encoded gamma glutamyl hydrolase can be assayed according to methods known in the art (see Wang et al. 1993).

Having identified the nucleic acid molecules encoding GH and methods for expressing the GH encoded thereby, the invention further provides a method of screening a substance for the ability of the substance to modify gamma glutamyl hydrolase function. The method comprises introducing a nucleic acid molecule encoding the GH into a host cell, and expressing the GH encoded by the molecule in the host cell. The cell is then exposed to a substance and evaluated to determine if the substance modifies the function of the GH. From this evaluation, substances effective in altering the function of the GH can be found. Such agents may be, for example, 4-fluoromethotrexate-glutamate (Johnson et al. 1994) or 6-deazo-5-oxo-norleucine (Waltham et al. 1996).

The evaluation of the cell to determine if the substance modifies the function of the GH can be by any means known in the art. The evaluation can comprise the direct monitoring of expression of gamma glutamyl hydrolase in the host cell (such as by the method disclosed herein), or the evaluation can be indirect and comprise the monitoring of hydrolysis of antifolylpolyglutamates by the gamma glutamyl hydrolase (such as by the method disclosed by Wang et al. 1993, Rhee et al. 1992, and Yao et al. 1995).

The nucleic acid molecules of the subject invention can be used either as probes or for the design of primers to obtain DNA encoding other GHs by either cloning and colony/plaque hybridization or amplification using the polymerase chain reaction (PCR).

Specific probes derived from SEQ ID NOs 1 or 3 can be employed to identify colonies or plaques containing cloned DNA encoding a member of the GH family using known methods (see Sambrook et al. 1989). One skilled in the art will recognize that by employing such probes under high stringency conditions (for example, hybridization at 42° C. with 5× SSPC and 50% formamide, washing at 50–65° C. with 0.5× SSPC), sequences having regions which are greater than 90% homologous or identical to the probe can be obtained. Sequences with lower percent homology or identity to the probe, which also encode GHs, can be obtained by lowering the stringency of hybridization and washing (e.g., by reducing the hybridization and wash temperatures or reducing the amount of formamide employed).

More particularly, in one embodiment, the method comprises selection of a DNA molecule encoding a GH, or a fragment thereof, the DNA molecule having a nucleotide sequence selected from the group consisting of SEQ ID NO:1 and SEQ ID NO:3, and designing an oligonucleotide probe for GH based on SEQ ID NO:1 or SEQ ID NO:3. A genomic or cDNA library of an organism is then probed with the oligonucleotide probe, and clones are obtained from the library that are recognized by the oligonucleotide probe so as to obtain DNA encoding another GH.

Specific primers derived from SEQ ID NOs 1 or 3 can be used in PCR to amplify a DNA sequence encoding a member of the GH family using known methods (see Innis et al. 1990). One skilled in the art will recognize that by employing such primers under high stringency conditions (for example, annealing at 50–60° C. depending on the length and specific nucleotide content of the primers employed), sequences having regions greater than 75% homologous or identical to the primers will be amplified.

More particularly, in a further embodiment the method comprises selection of a DNA molecule encoding GH, or a fragment thereof, the DNA molecule having a nucleotide sequence selected from the group consisting of SEQ ID NO:1 and SEQ ID NO:3, designing degenerate oligonucleotide primers based on regions of SEQ ID NO:1 or SEQ ID NO:3, and employing such primers in the polymerase chain reaction using as a template a DNA sample to be screened for the presence of GH-encoding sequences. The resulting PCR products can be isolated and sequenced to identify DNA fragments that encode polypeptide sequences corresponding to the targeted region of GH.

Various modifications of the nucleic acid and amino acid sequences disclosed herein are covered by the subject invention. These varied sequences still encode a functional GH.

The invention thus further provides an isolated nucleic acid molecule encoding a gamma glutamyl hydrolase, the nucleic acid molecule encoding a first amino acid sequence having at least 90% amino acid identity to a second amino acid sequence, the second amino acid sequence selected from the group consisting of SEQ ID NO:2 and SEQ ID NO:4.

The invention further provides an isolated DNA oligomer capable of hybridizing to the nucleic acid molecule encoding GH according to the subject invention. Such oligomers can be used as probes in a method of detecting the presence of GH in a sample. More particularly, a sample can be contacted with the DNA oligomer and the DNA oligomer will hybridize to any GH present in the sample, forming a complex therewith. The complex can then be detected, thereby detecting presence of GH in the sample.

The complex can be detected using methods known in the art. Preferably, the DNA oligomer is labeled with a detectable marker so that detection of the marker after the DNA oligomer hybridizes to any GH in the sample (wherein non-hybridized DNA oligomer has been washed away) is detection of the complex. Detection of the complex indicates the presence of GH in the sample. As will be readily apparent to those skilled in the art, such a method could also be used quantitatively to assess the amount of GH in a sample. Such a quantitative method could be especially useful in samples of cancerous tissue or serum of cancer patients, where the amount of GH present in the cancerous tissue or serum is indicative of the stage of the cancerous growth.

For detection, the oligomers can be labeled with, for example, a radioactive isotope, biotin, an element opaque to X-rays, or a paramagnetic ion. Radioactive isotopes are commonly used and are well known to those skilled in the art. Representative examples include indium-111, technetium-99m, and iodine-123. Biotin is a standard label which would allow detection of the biotin labeled oligomer with avidin. Paramagnetic ions are also commonly used and include, for example, chelated metal ions of chromium (III), manganese (II), and iron (III). When using such labels, the labeled DNA oligomer can be imaged using methods known to those skilled in the art. Such imaging methods include, but are not limited to, X-ray, CAT scan, PET scan, NMRI, and fluoroscopy. Other suitable labels include enzymatic labels (horseradish peroxidase, alkaline phosphatase, etc.) and fluorescent labels (such as FITC or rhodamine, etc.).

The invention further provides an antibody or fragment thereof specific for the gamma glutamyl hydrolase encoded by the nucleic acid molecules of the subject invention. Antibodies of the subject invention include polyclonal antibodies and monoclonal antibodies capable of binding to the GH, as well as fragments of these antibodies, and humanized forms. Humanized forms of the antibodies of the subject invention may be generated using one of the procedures known in the art such as chimerization. Fragments of the antibodies of the present invention include, but are not limited to, the Fab, the Fab2, and the Fd fragments.

The invention also provides hybridomas which are capable of producing the above-described antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (see Campbell 1984 and St. Groth et al. 1980). Any animal (mouse, rabbit, etc.) which is known to produce antibodies can be immunized with the antigenic GH (or an antigenic fragment thereof). Methods for immunization are well known in the art. Such methods include subcutaneous or intraperitoneal injection of the enzyme. One skilled in the art will recognize that the amount of the enzyme used for immunization will vary based on the animal which is immunized, the antigenicity of the enzyme, and the site of injection.

The enzyme which is used as an immunogen may be modified or administered in an adjuvant in order to increase the enzyme's antigenicity. Methods of increasing the antigenicity of an enzyme (i.e., a protein) are well known in the art and include, but are not limited to, coupling the antigen with a heterologous protein (such as a globulin or beta-galactosidase) or through the inclusion of an adjuvant during immunization.

For monoclonal antibodies, spleen cells from the immunized animals are removed, fused with myeloma cells, such as SP2/O-Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al. 1988).

Hybridomas secreting the desired antibodies are cloned and the class and subclass are determined using procedures known in the art (Campbell 1984).

For polyclonal antibodies, antibody containing antisera is isolated from the immunized animal and is screened for the presence of antibodies with the desired specificity using one of the above-described procedures.

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC or rhodamine, etc.), paramagnetic atoms, etc. Procedures for accomplishing such labeling are well known in the art, for example see Sternberger et al. 1970, Bayer et al. 1979, Engval et al. 1972, and Goding 1976.

The labeled antibodies or fragments thereof of the present invention can be used for in vitro, in vivo, and in situ assays to identify cells or tissues which express GH, to identify samples containing GH, or to detect the presence of GH in a sample. More particularly, the antibodies or fragments thereof can thus be used to detect the presence of GH in a sample, by contacting the sample with the antibody or fragment thereof. The antibody or fragment thereof binds to any GH present in the sample, forming a complex therewith. The complex can then be detected, thereby detecting the presence of GH in the sample. As will be readily apparent to those skilled in the art, such a method could also be used quantitatively to assess the amount of GH in a sample. Such a quantitative method could be especially useful in samples of cancerous tissue or serum of cancer patients, where the amount of GH present in the cancerous tissue or serum is indicative of the stage of the cancerous growth.

Fragments of the nucleic acid molecules encoding GH are also provided, and are best defined in the context of amino acid sequence relationships among members of the GH sequence family and information on the function of specific GH domains. A comparison of the amino acid sequence of SEQ ID NO:2 (human) with the amino acid sequence of SEQ ID NO:4 (rat) can identify an amino acid sequence that is conserved among GH family members. Antibodies prepared to the polypeptide encoded by this conserved fragment would therefore be expected to be of use as reagents capable of detecting many members of the GH family. Such antibodies, if introduced into cells that express GH, would also be expected to modify the normal function of the GHs expressed in those cells. In contrast, comparison of the amino acid sequence of SEQ ID NO:2 (human) with the amino acid sequence of SEQ ID NO:4 (rat) can identify an amino acid sequence that is less well conserved between the GHs. Antibodies prepared to the polypeptide encoded by this less well conserved fragment would therefore be expected to recognize selectively the GH from which the fragment was derived.

Since GH is involved in the hydrolysis of antifolylpolyglutamates, which are the result of the conversion of antifolates in cells, there are numerous uses of the subject invention. The invention thus further provides a method of decreasing deleterious side effects of antifolate treatment. The deleterious side effects of antifolate treatment stem primarily from the antifolylpolyglutamate conversion product of the. antifolates, and include the killing of bone marrow cells and gastrointestinal mucositis (Bertino 1993; Chu and Takamoto 1993). Since the gamma glutamyl hydrolase of the subject invention cleaves the antifolylpolyglutamates as indicated above, the antifolylpolyglutamates are reduced to less deleterious reaction products such as the original antifolate and glutamic acid. Thus, the method of decreasing deleterious side effects of antifolate treatment comprises increasing levels of GH in the desired cell (such as a bone marrow cell) of a patient receiving antifolates. The presence of increased levels of GH in the desired cell results in increased hydrolysis of antifolylpolyglutamates and thereby decreases the deleterious effects of the antifolate treatment.

As indicated above, levels of GH in a cell, such as a bone marrow cell, can be increased by introducing the nucleic acid molecule encoding GH into the cell and by expressing the GH encoded thereby. For in vivo expression of GH, various gene therapy techniques can be utilized to get the nucleic acid molecule into the desired cell. As should be readily apparent, the nucleic acid molecule encoding GH needs to be targeted to the desired cells (i.e., the bone marrow cells) by known methods, since in other cells of the patient decreased expression of GH may simultaneously or also be desirable.

The invention also provides a method of increasing the effectiveness of antifolate treatment which comprises decreasing levels of GH in the desired cell, such as a tumor cell of a patient receiving antifolates. Since the gamma glutamyl hydrolase of the subject invention cleaves the antifolylpolyglutamates as indicated above, the decreased levels of GH result in less cleavage (hydrolysis) of the antifolylpolyglutamates so that the effectiveness of the antifolate treatment is increased. Decreasing levels of GH allow greater amounts of antifolylpolyglutamates to function in the targeted cell.

As indicated above, levels of GH in a cell, such as a tumor cell, can be decreased by introducing an antisense or ribozyme construct into the cell. An antisense construct blocks translation of mRNA encoding GH into the GH enzyme. A ribozyme construct cleaves the mRNA encoding the GH thus also preventing expression of functional GH enzyme. For in vivo decreasing of expression of GH, various gene therapy techniques can again be utilized to introduce the antisense or ribozyme construct into the desired cell. The construct needs to be targeted to the desired cells (i.e., the tumor cells) by known methods, since in other cells of the patient increased expression of GH may simultaneously or also be desired (see above discussion in regard to bone marrow cells).

The effectiveness of antifolate treatment can also be increased by blocking the action of gamma glutamyl hydrolase in the desired cell (such as a tumor cell), thus also preventing hydrolysis of the antifolylpolyglutamates and increasing their effectiveness. Various methods for blocking the action of GH can be utilized, including the administration of a GH-blocking amount of a substance to the patient (the patient's tumor cells). Such substances can be identified according to the method of the subject invention, and preferably comprise peptide drug products and/or small molecules (Bevan et al. 1995; Sepetov et al. 1995; O'Connor et al. 1994; Rhee et al. 1995; Webber et al. 1993).

Drugs, such as peptide drugs, can be made using various methods known in the art. One such method utilizes the development of epitope libraries and biopanning of bacteriophage libraries. Briefly, attempts to define the binding sites for various monoclonal antibodies have led to the development of epitope libraries. Parmley and Smith developed a bacteriophage expression vector that could display foreign epitopes on its surface (Parmley and Smith 1988). This vector could be used to construct large collections of bacteriophage which could include virtually all possible sequences of a short (e.g. six-amino-acid) peptide. They also developed biopanning, which is a method for affinity-purifying phage displaying foreign epitopes using a specific antibody (see Parmley and Smith 1988; Cwirla et al. 1990; Scott and Smith 1990; Christian et al. 1992; Smith and Scott 1993).

After the development of epitope libraries, Smith et al. then suggested that it should be possible to use the bacteriophage expression vector and biopanning technique of Parmley and Smith to identify epitopes from all possible sequences of a given length. This led to the idea of identifying peptide ligands for antibodies by biopanning epitope libraries, which could then be used in vaccine design, epitope mapping, the identification of genes, and many other applications (Parmley and Smith 1988; Scott 1992).

Using epitope libraries and biopanning, researchers searching for epitope sequences found instead peptide sequences which mimicked the epitope, i.e., sequences which did not identify a continuous linear native sequence or necessarily occur at all within a natural protein sequence. These mimicking peptides are called mimotopes. In this manner, mimotopes of various binding sites/proteins have been found. LaRocca et al. (1992) expressed a mimotope of the human breast epithelial mucin tandem repeat in *Escherichia coli*. Balass et al. (1993) identified a hexapeptide that mimics a conformation-dependent binding site of the acetylcholine receptor. Hobart et al. (1993) isolated a mimotope that mimics the C6 epitope (the epitope for the sixth component of complement).

The sequences of these mimotopes, by definition, do not identify a continuous linear native sequence or necessarily occur in any way in a naturally-occurring molecule, i.e. a naturally occuring protein. The sequences of the mimotopes merely form a peptide which functionally mimics a binding site on a naturally-occurring protein. For example, the mimotope of Balass et al. (1993) mimics the binding site of the acetylcholine receptor.

Many of these mimotopes are short peptides. The availability of short peptides which can be readily synthesized in large amounts and which can mimic naturally-occurring sequences (i.e. binding sites) offers great potential application.

Using this technique, mimotopes to a monoclonal antibody that recognizes GH, or that recognize the antisense sequences for GH, can be identified. The sequences of these mimotopes represent short peptides which can then be used in various ways, for example as peptide drugs. Once the sequence of the mimotope is determined, the peptide drugs can be chemically synthesized.

The drugs, such as peptide drugs, disclosed herein, may be administered alone or in combination with compatible carriers as a composition. Compatible carriers include suitable pharmaceutical carriers or diluents. The diluent or carrier ingredients should be selected so that they do not diminish the therapeutic effects of the proteins, fragments, or drugs of the present invention.

The compositions herein may be made up in any suitable form appropriate for the desired use; e.g., oral, parenteral, or topical administration. Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art. Examples of parenteral administration are intraventricular, intracerebral, intramuscular, intravenous, intraperitoneal, rectal, and subcutaneous administration.

The subject invention also provides a method of monitoring the progression of a tumor by detecting the presence of GH associated with or secreted by the tumor. As indicated above, the presence of GH can be detected, for example, using an antibody or fragment thereof specific for GH or by using a DNA oligomer capable of hybridizing to nucleic acid molecules encoding the GH.

As discussed below, the GH molecule of the subject invention can include a leader sequence for targeting of the GH protein to the desired part of a cell. The leader nucleotide sequence of the rat GH is shown in SEQ ID NO:9 and encodes 24 amino acids (SEQ ID NO:10). The leader includes the ATG start codon encoding a methionine residue. The active form of the GH enzyme does not include the leader sequence, and therefore a conformational change likely occurs after cleavage of the leader peptide resulting in the mature enzyme. It should be readily apparent to those skilled in the art that a met residue may need to be added to the amino terminal of the amino acid sequence of the mature GH enzyme (i.e., added to SEQ ID NO:4) or an ATG added to the 5' end of the nucleotide sequence (i.e., added to SEQ ID NO:3), in order to express the enzyme in a host cell. The met version of the mature GH is thus specifically intended to be covered by reference to SEQ ID NO:4 or SEQ ID NO:3. It may be desirable when expressing the rat GH in a host cell to introduce a nucleotide sequence which includes the leader sequence (SEQ ID NO:9) and the rat GH encoding sequence (SEQ ID NO:3). After expression of the leader/rat GH fusion protein, the leader targets the rat GH protein within the cell before the leader peptide is cleaved from the mature rat GH protein. The amino acid sequence of the leader/rat GH fusion protein is shown in SEQ ID NO:12. SEQ ID NO:11 represents the entire open reading frame (ORF) of the rat GH and signal peptide, as well as the 5' and 3' untranslated regions. More particularly, nucleotides 1–5 of SEQ ID NO:11 are the Kozak sequence, and nucleotides 6–77 of SEQ ID NO:11 are the leader sequence. Nucleotides 78–959 of SEQ ID NO:11 encode the mature rat GH enzyme (with nucleotides 957–959 representing the TGA stop codon). The remaining nucleotides of SEQ ID NO:11 represent the 3' untranslated region.

The leader nucleotide sequence of the human GH is shown in SEQ ID NO:13 and encodes 24 amino acids (SEQ ID NO:14). The leader includes the ATG start codon encoding a methionine residue. The active form of the human GH enzyme, like the rat GH discussed above, also likely does not include the leader sequence. As with the rat GH, a met residue may need to be added to the amino terminal of the amino acid sequence of the mature human GH enzyme (i.e., added to SEQ ID NO:2) or an ATG added to the 5' end of the nucleotide sequence (i.e., added to SEQ ID NO:1), in order to express the enzyme in a host cell. The met version of the mature human GH is thus specifically intended to be covered by reference to SEQ ID NO:2 or SEQ ID NO:1. Furthermore, it may be that the leader sequence of the human GH extends to 25 amino acids (the 24 amino acids of SEQ ID NO:14 encoded by nucleotide SEQ ID NO:13 and the first arginine residue of SEQ ID NO:2 encoded by nucleotides 1–3 of SEQ ID NO:1). Reference to the leader sequence, such as by SEQ ID NO:13 or SEQ ID NO:14, is therefore intended to specifically also cover the sequence which is one amino acid or three nucleotides longer, and likewise reference to the mature enzyme, such as by SEQ ID NO:1 or SEQ ID NO:2, is intended to specifically also cover the sequence which is one amino acid or three nucleotides shorter. As with the rat GH, it may be desirable when expressing the human GH in a host cell to introduce a nucleotide sequence which includes the leader sequence (SEQ ID NO:13) and the human GH encoding sequence (SEQ ID NO:1). After expression of the leader/human GH fusion protein, the leader targets the human GH protein within the cell before the leader peptide is cleaved from the mature human GH protein. The amino acid sequence of the leader/human GH fusion protein is shown in SEQ ID NO:16. SEQ ID NO:15 represents the entire ORF of the human GH and signal peptide, as well as the 5' and 3' untranslated regions. More particularly, nucleotides 60–131 of SEQ ID NO:15 are the leader sequence, and nucleotides 132–1016 of SEQ ID NO:15 encode the mature human GH enzyme (with nucleotides 1014–1016 representing the TGA stop codon). Alternatively, nucleotides 60–134 of SEQ ID NO:15 may represent the leader sequence, with nucleotides 135–1016 encoding the mature human GH enzyme. The remaining nucleotides of SEQ ID NO:15 represent the 3' untranslated region.

MATERIALS AND METHODS

Cell culture

Rat H35 hepatoma cells (Wang et al. 1993; Rhee et al. 1993; Galivan and Rhee 1995; O'Connor et al. 1991; Yao et al. 1995; and Rhee et al. 1995) were cultured and transferred to serum free medium as previously described (Wang et al. 1993). The pooled medium was stored at −70° C. until used.

Purification of gamma glutamyl hydrolase

On the basis of the earlier study of Lin et al. (1993), the individual peaks from TSK-Gel Toyopearl butyl-650S (Wang et al. 1993) were further purified by chromatography on Matrix Gel Green A (Amicon Division, W.R. Grace & Co., Beverly Mass.). Up to 200 μg of protein was applied to a column (1×10 cm) of Matrix Green Gel A that had been equilibrated with 10 mM sodium acetate (pH 6.0) containing 0.1 mM zinc acetate and 50 mM β-mercaptoethanol. The column was washed with 40 mL of equilibration buffer and 40 mL of the same buffer containing 0.15 M sodium chloride. The enzyme was eluted with equilibration buffer containing 0.4 M sodium chloride and 10 mM octyl-β-glucoside. The specific activity of five independent preparations was 107,000 nmol/min-1/mg-1 with a S.D. of ±16%. The specific activity of each of the individual TSK butyl peaks fell within that range following purification on Matrix Green Gel A. GH was assayed as previously described (Wang et al. 1993) using 4-NH$_2$-10-CH$_3$PteGlu$_2$ (4-amino-10-methylpteroylglutamyl-gamma-glutamate) as substrate.

Microsequencing of Intact GH and Cyanogen Bromide Fragments

Purified enzyme was analyzed by SDS-10% polyacrylamide gel electrophoresis using a TRIS-Tricine buffer containing 0.3 mM thioglycolic acid in a Bio-Rad Mini Protean system. The gel was electroblotted (Bio-Rad Mini Trans-Blot apparatus) onto a PVDF membrane (Bio-Rad, Richmond Calif.) using 10 mM CAPS buffer, pH 11, containing 10% methanol and 4 mM dithioerythritol. The membrane was stained with 0.01% Coomassie Blue and the bands of interest excised and analyzed on an Applied Biosystems 477A sequencer. For internal sequencing, a single crystal of cyanogen bromide was added to a solution of purified enzyme (30–40 μg) in 70% trifluoroacetic acid and the solution heated at 45° C. for 45 min. The solution was lyophilized and fragments sequenced as above using a SDS-13% polyacrylamide gel.

Preparation of a polyclonal antibody to GH

A single rabbit was immunized with purified GH (an initial immunization of 50 μg, followed by 3 boosts of 50 μg each) using a standard protocol by Biodesign International (Kennebunk, Me.). The studies herein were done with an early test bleed, purified on Protein A-agarose, which had a 1 to 500,000 titer against 50 ng of purified GH in an ELISA assay.

EXAMPLE I

Cloning and Sequencing of Rat GH

The sequence of the open reading frame corresponding to gamma glutamyl hydrolase was determined using a combination of reverse transcription polymerase chain reaction (RT-PCR), rapid amplification of cDNA ends (RACE), and screening of a commercial cDNA library. Total cellular RNA was prepared from rat hepatoma H35 cells using TRI REAGENT (Molecular Research Center, Inc., Cincinnati Ohio), according to the manufacturer's instructions. Poly (A)$^+$ mRNA was isolated from total RNA by affinity chromatography using a spin column of microcrystalline oligo (dT) cellulose (New England Biolabs, Beverly Mass.). Poly (A)$^+$ mRNA eluate was precipitated with ethanol and stored at −70° C. for later use. The poly(A)$^+$ mRNA from H35 cells was reverse transcribed into cDNA using MMLV-reverse transcriptase and an oligo(dT) primer (Stratagene, Palo Alto, Calif.). The cDNA was subjected to PCR amplification using degenerate primers derived from the amino acid sequence of the N-terminus and of CNBr generated fragments. The primers used for RT-PCR were modified by carrying deoxyinosine residues at positions corresponding to ambiguous nucleotides (Ohtsuka et al. 1985). The RT-PCR generated a 605-base fragment denoted pGH-1.

The cDNA prepared from H35 mRNA was synthesized by MMLV reverse-transcriptase and ligated to the Marathon cDNA adaptor (Clontech, Palo Alto, Calif.). RACE ready cDNA was amplified with nested GH-specific primers in combination with Marathon adaptor primers, AP1 and AP2, respectively. For sequencing, PCR products generated with Taq polymerase were cloned into a PCR II vector in the TA Cloning system, as the 3' A overhangs are not removed (Invitrogen, San Diego, Calif.). The amount of PCR product needed to ligate with 50 ng of PCR II vector was estimated according to the manufacturer's directions.

A rat hepatoma cDNA library was obtained from Stratagene (Palo Alto, Calif.). A total of 10$^6$ λZAP II recombinant phage plaques on E. coli strain XL1-blue cells were screened. Phage plaques were lifted twice onto nitrocellulose membranes, denatured in 0.5 N NaOH/1.5 M NaCl, and neutralized in 1.5 M NaCl/1.0 M Tris HCl, pH 7.5. The membranes were baked for 2 h at 80° C. in a vacuum oven, and then prehybridized 16 h at 37° C. in prehybridization solution containing 5X SSC, SX Denhardt's, 0.1% SDS, 50% formamide, and 0.2 mg/mL salmon sperm DNA. This was followed by hybridization for 20 h in the above buffer with $^{32}$P-randomly-labelled pGH-1. Three partial cDNA's were obtained (pGH-3, pGH-4, and pGH-5).

cDNA inserts were excised from the λZAP II cDNA library and subcloned into pBluescript according to the in vivo excision procedure described by Stratagene. Plasmid DNA was prepared with a Wizard minipreps DNA purification system and used as a sequencing template. Initial sequencing for pGH-1 and pGH-2 was done using M13 forward and M13 reverse primers on the PCRII vector (Invitrogen). For the clones of pGH3, 4 and 5, T3 and T7 primers on pBluescript were used for determining the sequences at both ends of the insert. The dideoxynucleotide chain termination method of Sanger et al. (1977) was used with sequenase (USB). Primers were synthesized by the Molecular Genetic Core at the Wadsworth Center (Albany N.Y.).

EXAMPLE II

Purification of Rat GH

Rat GH was previously shown to elute in three peaks of activity from butyl—TSK chromatography (Wang et al. 1993). These three peaks (peaks 1, 2, and 3) have now been individually purified to homogeneity by chromatography on Matrix Green Gel A. Each peak when purified appeared as a single diffuse band of $M_r$ about 55 kDa on SDS-polyacrylamide gel electrophoresis. The broad appearance of these bands and the binding of the enzyme to lentil lectin affinity columns (Wang et al. 1993) indicated that GH was a glycoprotein. Owing to the limited amounts of enzyme available and the difficulty in eliminating impurities consistently from peak 3, peaks 1 and 2 were routinely pooled, purified by Matrix Green Gel A chromatography, and utilized experimentally. After treatment with the enzyme PNGase (peptide-N$^4$-(N-acetyl-β-D-glucosaminyl) asparagine amidase), which cleaves Asn linked carbohydrate from glycoproteins (Tarentino and Plummer 1994), the enzyme appeared as two discrete bands with molecular weights of approximately 33 and 35-kDa, suggesting that the protein is highly glycosylated, primarily at Asn. Both deglycosylated forms were identified as GH because their N-terminal sequences were identical to that of the 55 kDa band. A polyclonal antibody raised in rabbits to combined purified peaks 1 and 2 detected the 55-kDa glycosylated form in western blots and the two deglycosylated forms of GH. The antibody captured the enzyme activity in a sandwich type assay verifying its specificity. Although combined peaks 1 and 2 were used, replication of the experiment with each of the purified individual peaks gave similar results.

EXAMPLE III
Sequencing of Intact Rat GH and Cyanogen Bromide Fragments of Rat GH The N-terminal sequences of the Matrix Green Gel A purified combined Peaks 1+2 and purified peak 3 were found to be identical (SEQ ID NO:5: G S Y E R G S K R P I I G I I). Peak 3 was purified separately because it yielded one or two contaminating proteins in many of its preparations. Cyanogen bromide digestion of either combined peaks 1+2 or peak 3 yielded two fragments (designated band 3 and band 4) with molecular weights less than 10 kDa. The N-terminal sequence of band 3 from either combined peaks 1+2 or peak 3 was the same (SEQ ID NO:6: F R N L P E E L L N). The N-terminal sequence of band 4 from purified peak 3 was SEQ ID NO:7: E G Y D Y P I Y A V, while the same band from combined peaks 1+2 had E instead of D at position 4 (SEQ ID NO:8). There was some ambiguity assigning the residue at position 4 because significant amounts of lysine were also determined at this position. The identical N-terminal and internal structural sequences of combined peaks 1+2 and peak 3 along with the amino acid analysis (Table 1) and immunoreactivity suggested extensive amino acid sequence similarity of the three peaks from butyl TSK chromatography. Analysis of GH from rat hepatocyte and human cell lines (MCF7, HL60, and HEPG2) by hydrophobic chromatography resulted in a single peak of enzyme activity. These results suggest that the apparent heterogenity of GH from H35 cells on hydrophobic chromatography may be unique and related to its extensive glycosylation.

EXAMPLE IV
Cloning and Sequencing Strategy for a cDNA Coding for Rat GH

Portions of the N-terminal sequence and one internal sequence from purified peak 3 were used to construct primers for RT-PCR. This produced a cDNA fragment (pGH1) composed of bases 100 through 705. This fragment contained a nucleotide sequence encoding the protein sequence of band 3. Screening of a commercial cDNA library using this RT-PCR product identified three clones containing cDNA consisting of bases 347–1096 (pGH3) and bases 1–902 (pGH4/5). Using the technique of 3'-RACE (see Materials and Methods), a cDNA fragment was obtained which contained the complete 3' end of the coding region. A full length cDNA for the GH coding region (SEQ ID NO:3) was prepared by PCR amplification using poly (A)$^+$ mRNA from H35 cells and primers that flanked the coding region. The full length cDNA consisted of 1,204 nucleotides (which includes the leader sequence and the 5' and 3' untranslated regions). The first 5 nucleotides of the 5' end of the sequence correspond to part of a consensus sequence for the initiation of translation in vertebrates (Kozak 1987).

EXAMPLE V
Characteristics of the Encoded Rat GH

The full length cDNA coded for a protein of 317 amino acids (SEQ ID NO:12). Based on the N-terminal sequence of the purified enzyme, this includes a leader sequence (nucleotide SEQ ID NO:9 and amino acid SEQ ID NO:10) with Gly-25 as the N-terminus of the mature enzyme (Gly-25 of SEQ ID NO:12). The calculated molecular weight of the mature protein was 33,400 kDa, which is within the range of the deglycosylated proteins. The calculated amino acid analysis of the protein was consistent with the determined amino acid composition of the purified enzyme (Table 1). The deduced amino acid sequence of the GH (SEQ ID NO:4) contained seven potential N-linked glycosylation sites (Winzler 1973), supporting the observation that the protein is highly glycosylated. There are three Cys residues in the sequence. The finding that the enzyme activity of GH is enhanced by the presence of sulfhydryl-containing compounds (Wang et al. 1993) and the observed inhibition of GH by iodoacetic acid suggest that the enzyme may contain an active site or structurally critical cysteine.

EXAMPLE VI
Human GH

Using the full-length cDNA of rat GH (SEQ ID NO:11) as a query sequence, the database searching program BLAST from the Wisconsin Genetics Groups (Madison, Wis.) was used for a sequence homology search. Two clones with GenBank ID R07771 and H09442 were identified from the database of human Expressed Sequence Tags (ESTs) with 80 and 75% homology, respectively, to the rat GH cDNA sequence. The insert sizes for R07771 is 0.8 kb and for H09442 is 1.3 kb. The cDNA for clone R07771 was isolated from female placenta and for H09442 was from infant brain. The two human EST clones were obtained from Genome Systems Inc. (St. Louis, Mo.). The initial sequencing for clone R07771 was done using T3 and T7 primers on the pT7T3D-Pac vector and for clone H09442 using M13R and M13F primers on the Lafmid BA vector by the method of Sanger et al. (1977) using Sequenase 2 (USB). Primers were synthesized by the Molecular Core Facility at WCLR.

The sequence homology between rat GH and these human EST clones was further confirmed with deduced amino acid sequences. The FRAMESEARCH program was used to identify possible open reading frames (ORFs) for the human clones. The data showed that clone R07771 had an ORF from nucleotide number 2 to 302 and an ORF for H09442 is from nucleotide number 59 to 348. Using the PILEUP program the deduced human amino acid sequences were aligned and compared to rat GH. The amino acid sequence of clone R07771 showed a 75% identity to rat GH at amino acid number 153 to 253 and clone H09442 was 76.8% homologous to the 5' end of rat GH. These results strongly suggest that the two ESTs identified were parts of the human homolog to GH.

The 5' sequence of clone R07771 overlaps with H09442 at nucleotide number 518. Sequencing for the entire full length insert was done using GH specific primers synthesized by the Molecular Core Facility at WCLR. The nucleotide sequence of the full length cDNA for human GH is shown in SEQ ID NO:15 (which includes the leader sequence and the 5' and 3' untranslated regions). The amino acid sequence of the full length human GH is shown in SEQ ID NO:16. Amino acid sequence comparison of the full length GH between rat and human showed 67.3% identity. The leader sequence of the human GH is shown in SEQ ID NO:13 (nucleotide) and SEQ ID NO:14 (amino acid). SEQ ID NOs: 1 and 2 show the mature human GH enzyme nucleotide and amino acid sequences, respectively.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

Amino Acid Composition of the Purified Peaks from Butyl TSK Chromatography of Rat Gamma Glutamyl Hydrolase

| Amino Acid | Theoretical[a] | Peak 1 | Peak 2 | Peak 3 |
|---|---|---|---|---|
| Asp + Asn | 30 | 30.99 | 30.47 | 28.41 |
| Thr | 17 | 17.16 | 15.92 | 16.1 |
| Ser | 26 | 21.8 | 21.29 | 26.6 |
| Glu + Gln | 29 | 32.6 | 32.5 | 29.4 |
| Pro | 11 | 5.33 | 4.93 | 4.76 |
| Gly | 18 | 14.57 | 21.55 | 26.17 |
| Ala | 17 | 17.47 | 19.63 | 19.86 |
| Cys | 3 | nd | nd | nd |
| Val | 14 | 14.83 | 14.69 | 14.35 |
| Met | 5 | 4.82 | 5.91 | 6.54 |
| Ile | 16 | 15.64 | 16.33 | 16.1 |
| Leu[b] | 30 | 40.06 | 36.10 | 36.22 |
| Tyr | 14 | 11.59 | 8.78 | 7.81 |
| Phe | 22 | 22.1 | 23.21 | 19.86 |
| Lys | 20 | 20.20 | 18.83 | 18.37 |
| His | 6 | 6.91 | 6.31 | 6.28 |
| Trp | 4 | nd | nd | nd |
| Arg | 11 | 10.76 | 10.44 | 10.07 | nd - not determined;
[a] - Calculated amino acid composition of the translated cDNA sequence corresponding to gamma glutamyl hydrolase expressed as number of amino acid residues per mol of enzyme
[b] - Glucosamine coelutes with leucine on this amino acid analyzer resulting in potential falsely elevated leucine values.

LIST OF REFERENCES CITED

Baggott, J. E., et al., *Am J Clin Nutr* 46:295–301 (1987).
Balass, M., et al., *Proc Natl Acad Sci USA* 90:10638–10642 (1993).
Bayer, E. A., et al., *Meth Enzym* 62:308 (1979).
Bertino, J. R., *J Clin Oncol* 11:5–14 (1993).
Bevan, P., et al., *Trends in Biotechnology* 13(3):115–121 (1995).
Bhandari, S. D., et al., *J Nutr* 120:467–475 (1990).
Bordo, D. and Argos, P., *J Mol Biol* 217:721–729 (1991).
Campbell, A. M., *Monoclonal Antibody Technology: Laboratory Techniques in Biochemistry and Molecular Biology*, Elsevier Science Publishers, Amsterdam, The Netherlands (1984).
Capecchi, M., *Cell* 22:479–488 (1980).
Chandler, C. J., et al., *J Biol Chem* 261:928–933 (1986).
Chrisey, L., et al., *Antisense Research and Development* 1(1):57–63 (1991).
Christian, R. B., et al., J Mol Biol 227:711–718 (1992).
Christoffersen, R. E. and Marr, J. J., *Journal of Medicinal Chemistry* 38(12):2023–2037 (1995).
Chu, E. and Takamoto, C. H., in *Principle and Practice of Oncology*, DeVito et al., eds., J. B. Lippincott and Co., Philadelphia Pa., pp. 358–374 (1993).
Cwirla, S. E., et al., *Proc Natl Acad Sci USA* 87:6378–6382 (1990).
Elsenhans, B., et al., *J Biol Chem* 259:6364–6368 (1984).
Engval, E., et al., *Immunol* 109:129 (1972).
Fleming, G. and Schilsky, R. L., Seminar in Oncology 19:707–719 (1992).
French, S. and Robson, B., *J Molecular Evolution* 19:171–175 (1983).
Galivan, J. and Rhee, M. S., *Biochem Pharmacol* 50:1659–1663 (1995).
Goding, J. W., *J Immunol Meth* 13:215 (1976).
Han, L., et al., *Proc Natl Acad Sci USA* 88:4313–4317 (1991).
Hobart, M. J., et al., *Proc R Soc London B* 252:157–162 (1993).
Horne, D. W., et al., *J Nutr* 111:442–449 (1981).
Innis, et al., *PCR Protocols*, Academic Press, San Diego, Calif. (1990).
Johnson, T. B., et al., *Cell Pharmacol* 1:82–86 (1994).
Klein, T. M., et al., *Nature* 327:70–73 (1987).
Kozak, M., *Nucleic Acid Res* 15:8125–8148 (1987).
Krumdieck, C. L., et al.,*Am J Clin Nutr* 28:530–534 (1975).
LaRocca, D., et al., *Hybridoma* 11:191–201 (1992).
Lin, S., et al., *Phytochemistry* 32:1109–1117 (1993).
Lutz, et al., *Exp Cell Res* 175:109–124 (1988).
Mannino, R. J. and Gould-Fogerite, S., *BioTechniques* 6:682–690 (1988).
McGuire, J. J. and Coward, J. K., in *Folates and Pterins: Vol 1 Chemistry and Biochemistry of folates* (Blakley, R. L., and Benkovic, S. J., eds.) John Wiley & Sons, Inc., New York, pp 135–190 (1984).
Miller, L. K., *Bioessays* 11:91–95 (1989).
O'Connor, B. M., et al., *Cancer Res* 51:3874–3881 (1991).
O'Connor, B., et al., *Cancer Chemother Pharmacol* 34:225–229 (1994).
Ohtsuka, E., et al., *J Biol Chem* 260:2605–2608 (1985).
Parmley, S. F. and Smith, G. P., *Gene* 73:305–318 (1988).
Pizzorno, G., et al., *Cancer Res* 55:566–573 (1995).
Priest, D. G., et al., *Mol Cell Biochem* 43:81–87 (1982).
Rao, K. N., and Noronha, J. M., *Biochim Biophys Acta* 481:594–607 (1977).
Reisenauer, A. M., et al., *Science* 198:196–197 (1977).
Rhee, M., et al., *Mol Pharm* 42:909–916 (1992).
Rhee, M. S., et al., *Cancer Res* 53:2227–2230 (1993).
Rhee, M., et al., *Pharmacol* 2:97–101 (1995).
Rhee, M. S., et al., *Cellular Pharmacol* 2:289–292 (1995).
Rosenberg, I. H. and Neuman, H., *J Biol Chem* 249:5126–5130 (1974).
Rossi, J. J., et al., *AIDS Research and Human Retroviruses* 8(2):183–189 (1992).
Rossi, J. J., *British Medical Bulletin* 51(1):217–225 (1995).
Saini, P. K., and Rosenberg, I. H., *J Biol Chem* 249:5131–5134 (1974).
Sambrook et al., *Molecular Cloning: A Laboratory Manual*, 2d Edition, Cold Spring Harbor Laboratory Press, Cold Spring Harbor, N.Y. (1989).
Samuels, L. L., et al., *Cancer Res* 46:2230–2235 (1986).
Sanger, F., et al., *Proc Natl Acad Sci USA* 74:5463–5467 (1977).
Sarver, N., et al., *Science* 247:1222–1225 (1990).
Scott, J. K., *Trends in Biochem Sci* 17:241–245 (1992).
Scott, J. K. and Smith, G. P., *Science* 249:386–390 (1990).
Sepetov, N. F., et al., *Proc Natl Acad Sci USA* 92:5426–5430 (1995).
Shigekawa, K. and Dower, W. J., *BioTechniques* 6:742–751 (1988).
Shin, Y. S., et al., *Arch Biochem Biophys* 163:211–224 (1974).
Silink, M., et al., *J Biol Chem* 250:5982–5994 (1975).
Smith, G. P. and Scott, J. K., *Methods in Enzymology* 217:228–257 (1993).
Sternberger, L. A., et al., *J Histochem Cytochem* 18:315 (1970).
St. Groth, et al., *J Immunol Methods* 35:1–21 (1980).
Stokstad, E. L. and Koch, J., *Physiol Rev* 47:83–116 (1967).
Tarentino, A. and Plummer, T. H., Jr., *Methods Enzymol* 230:44–57 (1994).
Taylor, W. R., *J Theor Biol* 119:205–218 (1986).
Waltham, M., et al., *Proceed Amer Assoc Can Res* 37:2620, abstract (1996).

Wang, et al., *J Biol Chem* 261:13551–13555 (1986).
Wang, et al., *Biochim Biophys Acta* 1164:227–235 (1993).
Wang, et al., in *Chemistry and Bioloqy of Pteridines and Folates*, Ayling et al., eds., Plenum Press, New York pp. 655–658 (1993).

Webber, G., et al., *J Med Chem* 36:733–746 (1993).
Winzler, R. J., "The chemistry of glycoproteins" in *Hormonal Proteins and Peptides* (ed Li, C. H.) Academic Press, New York p 1–15 (1973).
Yao, R., et al., *Mol Pharmacol* 48:505–511 (1995).

What is claimed is:

1. An antibody or fragment thereof specific for an intracellular human or rat gamma glutamyl hydrolase.

2. The antibody of claim 1 wherein said antibody comprises a monoclonal antibody.

3. The antibody of claim 1 wherein said antibody comprises a polyclonal antibody.

4. A method of detecting presence of an intracellular human or rat gamma glutamyl hydrolase in a sample, said method comprising:

contacting a sample with the antibody or fragment thereof of claim 1, wherein said antibody or fragment thereof binds to any of said intracellular human or rat gamma glutamyl hydrolase present in said sample, forming a complex therewith; and detecting said complex, thereby detecting presence of an intracellular human or rat gamma glutamyl hydrolase in said sample.

5. The method of claim 4 wherein said antibody or fragment thereof is labeled with a detectable marker.

6. A method of monitoring progression of a tumor, said method comprising detecting presence of intracellular human or rat gamma glutamyl hydrolase associated with or secreted by said tumor, wherein said intracellular human or rat gamma glutamyl hydrolase is detected using the antibody or fragment thereof of claim 1.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 885 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
AGACCCCACG GCGACACCGC CAAGAAGCCC ATCATCGGAA TATTAATGCA AAAATGCCGT      60

AATAAAGTCA TGAAAAACTA TGGAAGATAC TATATTGCTG CGTCCTATGT AAAGTACTTG     120

GAGTCTGCAG GTGCGAGAGT TGTACCAGTA AGGCTGGATC TTACAGAGAA AGACTATGAA     180

ATACTTTTCA AATCTATTAA TGGAATCCTT TTCCCTGGAG GAAGTGTTGA CCTCAGACGC     240

TCAGATTATG CTAAAGTGGC CAAAATATTT TATAACTTGT CCATACAGAG TTTTGATGAT     300

GGAGACTATT TTCCTGTGTG GGGCACATGC CTTGGATTTG AAGAGCTTTC ACTGCTGATT     360

AGTGGAGAGT GCTTATTAAC TGCCACAGAT ACTGTTGACG TGGCAATGCC GCTGAACTTC     420

ACTGGAGGTC AATTGCACAG CAGAATGTTC CAGAATTTTC CTACTGAGTT GTTGCTGTCA     480

TTAGCAGTAG AACCTCTGAC TGCCAATTTC CATAAGTGGA GCCTCTCCGT GAAGAATTTT     540

ACAATGAATG AAAAGTTAAA GAAGTTTTTC AATGTCTTAA CTACAAATAC AGATGGCAAG     600

ATTGAGTTTA TTTCAACAAT GGAAGGATAT AAGTATCCAG TATATGGTGT CCAGTGGCAT     660

CCAGAGAAAG CACCTTATGA GTGGAAGAAT TTGGATGGCA TTTCCCATGC ACCTAATGCT     720

GTGAACCCCG CATTTTATTT AGCAGAGTTT TTTGTTAATG AAGCTCGGAA AAAGAACCAT     780

CATTTTAAAT CTGAATCTGA AGAGGAGAAA GCATTGATTT ATCAGTTCAG TCCAATTTAT     840

ACTGGAAATA TTTCTTCATT TCAGCAATGT TACATATTTG ATTGA                     885
```

(2) INFORMATION FOR SEQ ID NO:2:

(i) SEQUENCE CHARACTERISTICS:
      (A) LENGTH: 294 amino acids
      (B) TYPE: amino acid
      (C) STRANDEDNESS: Not Relevant
      (D) TOPOLOGY: linear (ii) MOLECULE TYPE: protein (xi) SEQUENCE DESCRIPTION: SEQ ID NO:2:

```
Arg Pro His Gly Asp Thr Ala Lys Lys Pro Ile Ile Gly Ile Leu Met
1               5                   10                  15

Gln Lys Cys Arg Asn Lys Val Met Lys Asn Tyr Gly Arg Tyr Tyr Ile
            20                  25                  30

Ala Ala Ser Tyr Val Lys Tyr Leu Glu Ser Ala Gly Ala Arg Val Val
        35                  40                  45

Pro Val Arg Leu Asp Leu Thr Glu Lys Asp Tyr Glu Ile Leu Phe Lys
```

```
            50                  55                  60
Ser Ile Asn Gly Ile Leu Phe Pro Gly Gly Ser Val Asp Leu Arg Arg
 65                  70                  75                  80

Ser Asp Tyr Ala Lys Val Ala Lys Ile Phe Tyr Asn Leu Ser Ile Gln
                 85                  90                  95

Ser Phe Asp Asp Gly Asp Tyr Phe Pro Val Trp Gly Thr Cys Leu Gly
                100                 105                 110

Phe Glu Glu Leu Ser Leu Leu Ile Ser Gly Glu Cys Leu Leu Thr Ala
            115                 120                 125

Thr Asp Thr Val Asp Val Ala Met Pro Leu Asn Phe Thr Gly Gly Gln
            130                 135                 140

Leu His Ser Arg Met Phe Gln Asn Phe Pro Thr Glu Leu Leu Leu Ser
145                 150                 155                 160

Leu Ala Val Glu Pro Leu Thr Ala Asn Phe His Lys Trp Ser Leu Ser
                165                 170                 175

Val Lys Asn Phe Thr Met Asn Glu Lys Leu Lys Lys Phe Phe Asn Val
                180                 185                 190

Leu Thr Thr Asn Thr Asp Gly Lys Ile Glu Phe Ile Ser Thr Met Glu
                195                 200                 205

Gly Tyr Lys Tyr Pro Val Tyr Gly Val Gln Trp His Pro Glu Lys Ala
210                 215                 220

Pro Tyr Glu Trp Lys Asn Leu Asp Gly Ile Ser His Ala Pro Asn Ala
225                 230                 235                 240

Val Asn Pro Ala Phe Tyr Leu Ala Glu Phe Phe Val Asn Glu Ala Arg
                245                 250                 255

Lys Lys Asn His His Phe Lys Ser Glu Ser Glu Glu Lys Ala Leu
                260                 265                 270

Ile Tyr Gln Phe Ser Pro Ile Tyr Thr Gly Asn Ile Ser Ser Phe Gln
            275                 280                 285

Gln Cys Tyr Ile Phe Asp
    290
```

(2) INFORMATION FOR SEQ ID NO:3:

(i) SEQUENCE CHARACTERISTICS:
        (A) LENGTH: 882 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GGATCCTATG AGCGCGGCTC CAAGCGTCCC ATCATCGGAA TAATAATGCA AGAATGTTAT      60

GGGAACATGA CGAAGTTGGG AAGATTCTAC ATTGCTGCGT CCTATGTGAA GTTTATAGAG     120

TCTGCGGGTG CAAGAGTCGT GCCCATAAGG CTCGACCTTA ATGATGCACA GTATGAAACA     180

CTTTTTAGAT CTATTAATGG AGTCCTCTTG CCTGGAGGGG GTGCTAACCT AACACATTCA     240

GGTTATTCCC GTGTGGCCAA AATATTTTTC ACCAAGGCTC TAGAGAGTTT TGATAATGGA     300

GACTATTTTC CTGTGTGGGG AACATGCCTG GGATTGGAGG AGCTTTCCGT CCTGGTTAGT     360

AATGACAACT TACTGACACT CACAAACACC AGCTCAGTGA AATTGCCTTT GAACTTCACG     420

AGAGATTCAA AGCAGAGCAG AATGTTCCGG AATCTTCCTG AGGAGTTATT GAATTCATTA     480

GCATCAGAAA ATCTGACTGC AAATTTTCAC AAGTGGAGCC TGTCTGTGAA GAACTTTACA     540

GAAAACGAGA AGTTAAAGAA GTTTTTCAAT ATATTAACAG TCAATACAGA TGGCAAGACT     600
```

```
GAGTTCATTT CATCCATGGA AGGATATAAG TATCCAATAT ATGCTGTCCA GTGGCATCCT      660

GAGAAAGCAC CATTTGAGTG AAGAAACTG CGAGGCATTT CCCATGCACC GAATGCTGTG       720

AAGACTTCAT TTTACTTAGC AAAATTTTTT ATTTCTGAAG CTCTGAAAAA TGATCACCAC      780

TTTGAGAACG AACTTGAAGA GACTGAATCC TTGATTTACC AGTTCTGTCC AGTTTATACT      840

GGAAATATTT CTTCATTTCA GCAAGCTTAT ATGTTTAACT GA                         882
```

(2) INFORMATION FOR SEQ ID NO:4:

(i) SEQUENCE CHARACTERISTICS:
        (A) LENGTH: 293 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:4:

```
Gly Ser Tyr Glu Arg Gly Ser Lys Arg Pro Ile Ile Gly Ile Ile Met
1               5                   10                  15

Gln Glu Cys Tyr Gly Asn Met Thr Lys Leu Gly Arg Phe Tyr Ile Ala
            20                  25                  30

Ala Ser Tyr Val Lys Phe Ile Glu Ser Ala Gly Ala Arg Val Val Pro
        35                  40                  45

Ile Arg Leu Asp Leu Asn Asp Ala Gln Tyr Glu Thr Leu Phe Arg Ser
50                  55                  60

Ile Asn Gly Val Leu Leu Pro Gly Gly Ala Asn Leu Thr His Ser
65                  70                  75                  80

Gly Tyr Ser Arg Val Ala Lys Ile Phe Phe Thr Lys Ala Leu Glu Ser
                85                  90                  95

Phe Asp Asn Gly Asp Tyr Phe Pro Val Trp Gly Thr Cys Leu Gly Leu
            100                 105                 110

Glu Glu Leu Ser Val Leu Val Ser Asn Asp Asn Leu Leu Thr Leu Thr
        115                 120                 125

Asn Thr Ser Ser Val Lys Leu Pro Leu Asn Phe Thr Arg Asp Ser Lys
130                 135                 140

Gln Ser Arg Met Phe Arg Asn Leu Pro Glu Glu Leu Leu Asn Ser Leu
145                 150                 155                 160

Ala Ser Glu Asn Leu Thr Ala Asn Phe His Lys Trp Ser Leu Ser Val
                165                 170                 175

Lys Asn Phe Thr Glu Asn Glu Lys Leu Lys Lys Phe Asn Ile Leu
            180                 185                 190

Thr Val Asn Thr Asp Gly Lys Thr Glu Phe Ile Ser Ser Met Glu Gly
        195                 200                 205

Tyr Lys Tyr Pro Ile Tyr Ala Val Gln Trp His Pro Glu Lys Ala Pro
210                 215                 220

Phe Glu Trp Lys Lys Leu Arg Gly Ile Ser His Ala Pro Asn Ala Val
225                 230                 235                 240

Lys Thr Ser Phe Tyr Leu Ala Lys Phe Ile Ser Glu Ala Leu Lys
                245                 250                 255

Asn Asp His His Phe Glu Asn Glu Leu Glu Glu Thr Glu Ser Leu Ile
            260                 265                 270

Tyr Gln Phe Cys Pro Val Tyr Thr Gly Asn Ile Ser Ser Phe Gln Gln
        275                 280                 285

Ala Tyr Met Phe Asn
        290
```

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:5:

```
Gly Ser Tyr Glu Arg Gly Ser Lys Arg Pro Ile Ile Gly Ile Ile
1               5                   10                  15
```

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:6:

```
Phe Arg Asn Leu Pro Glu Glu Leu Leu Asn
1               5                   10
```

(2) INFORMATION FOR SEQ ID NO:7:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:7:

```
Glu Gly Tyr Asp Tyr Pro Ile Tyr Ala Val
1               5                   10
```

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:8:

```
Glu Gly Tyr Glu Tyr Pro Ile Tyr Ala Val
1               5                   10
```

(2) INFORMATION FOR SEQ ID NO:9:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
ATGGCAAGCC TGGGCCGCCT GCTGTGCGCA TGGGTTTTGC TGCTGTGCGG GCTTGCAAGC    60
CCCGGGCTGT CC                                                        72
```

(2) INFORMATION FOR SEQ ID NO:10:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:10:

```
Met Ala Ser Leu Gly Arg Leu Leu Cys Ala Trp Val Leu Leu Leu Cys
1               5                   10                  15

Gly Leu Ala Ser Pro Gly Leu Ser
            20
```

(2) INFORMATION FOR SEQ ID NO:11:

(i) SEQUENCE CHARACTERISTICS:
        (A) LENGTH: 1204 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
CCGCGATGGC AAGCCTGGGC CGCCTGCTGT GCGCATGGGT TTTGCTGCTG TGCGGGCTTG    60
CAAGCCCCGG GCTGTCCGGA TCCTATGAGC GCGGCTCCAA GCGTCCCATC ATCGGAATAA   120
TAATGCAAGA ATGTTATGGG AACATGACGA AGTTGGGAAG ATTCTACATT GCTGCGTCCT   180
ATGTGAAGTT TATAGAGTCT GCGGGTGCAA GAGTCGTGCC CATAAGGCTC GACCTTAATG   240
ATGCACAGTA TGAAACACTT TTTAGATCTA TTAATGGAGT CCTCTTGCCT GGAGGGGGTG   300
CTAACCTAAC ACATTCAGGT TATTCCCGTG TGGCCAAAAT ATTTTTCACC AAGGCTCTAG   360
AGAGTTTTGA TAATGGAGAC TATTTTCCTG TGTGGGAAC ATGCCTGGGA TTGGAGGAGC    420
TTTCCGTCCT GGTTAGTAAT GACAACTTAC TGACACTCAC AAACACCAGC TCAGTGAAAT   480
TGCCTTTGAA CTTCACGAGA GATTCAAAGC AGAGCAGAAT GTTCCGGAAT CTTCCTGAGG   540
AGTTATTGAA TTCATTAGCA TCAGAAAATC TGACTGCAAA TTTTCACAAG TGGAGCCTGT   600
CTGTGAAGAA CTTTACAGAA AACGAGAAGT TAAAGAAGTT TTTCAATATA TTAACAGTCA   660
ATACAGATGG CAAGACTGAG TTCATTTCAT CCATGGAAGG ATATAAGTAT CCAATATATG   720
CTGTCCAGTG GCATCCTGAG AAAGCACCAT TTGAGTGGAA GAAACTGCGA GGCATTTCCC   780
ATGCACCGAA TGCTGTGAAG ACTTCATTTT ACTTAGCAAA ATTTTTTATT TCTGAAGCTC   840
TGAAAAATGA TCACCACTTT GAGAACGAAC TTGAAGAGAC TGAATCCTTG ATTTACCAGT   900
TCTGTCCAGT TTATACTGGA AATATTTCTT CATTTCAGCA AGCTTATATG TTTAACTGAA   960
AGACTTCAAT ATGGTAACAG AGCAACTTTG AGTAATTCCG TGATTGAATT GCTAACACTG  1020
CTCAGGGCAG TGTGAGAAAG CCACACAGAT GCCTTTGCTG TGTGCCTGGT TCTGATTCAT  1080
GGCTTAATAA TGATTATTTT TATCAGATTT GATAACCCGA CAATGAAAAA GATAAAAAAA  1140
AATCATAGTG TTTTTAGTGA AAATGCCTTC TTAGGTCTGA AGATTCTAAA AATACAAGTT  1200
TTTG                                                               1204
```

(2) INFORMATION FOR SEQ ID NO:12:

(i) SEQUENCE CHARACTERISTICS:
        (A) LENGTH: 317 amino acids (B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:12:

```
Met Ala Ser Leu Gly Arg Leu Leu Cys Ala Trp Val Leu Leu Leu Cys
1               5                   10                  15

Gly Leu Ala Ser Pro Gly Leu Ser Gly Ser Tyr Glu Arg Gly Ser Lys
            20                  25                  30

Arg Pro Ile Ile Gly Ile Ile Met Gln Glu Cys Tyr Gly Asn Met Thr
            35                  40                  45

Lys Leu Gly Arg Phe Tyr Ile Ala Ala Ser Tyr Val Lys Phe Ile Glu
50                      55                  60

Ser Ala Gly Ala Arg Val Val Pro Ile Arg Leu Asp Leu Asn Asp Ala
65                  70                  75                  80

Gln Tyr Glu Thr Leu Phe Arg Ser Ile Asn Gly Val Leu Leu Pro Gly
                85                  90                  95

Gly Gly Ala Asn Leu Thr His Ser Gly Tyr Ser Arg Val Ala Lys Ile
            100                 105                 110

Phe Phe Thr Lys Ala Leu Glu Ser Phe Asp Asn Gly Asp Tyr Phe Pro
            115                 120                 125

Val Trp Gly Thr Cys Leu Gly Leu Glu Glu Leu Ser Val Leu Val Ser
130                 135                 140

Asn Asp Asn Leu Leu Thr Leu Thr Asn Thr Ser Ser Val Lys Leu Pro
145                 150                 155                 160

Leu Asn Phe Thr Arg Asp Ser Lys Gln Ser Arg Met Phe Arg Asn Leu
                165                 170                 175

Pro Glu Glu Leu Leu Asn Ser Leu Ala Ser Glu Asn Leu Thr Ala Asn
            180                 185                 190

Phe His Lys Trp Ser Leu Ser Val Lys Asn Phe Thr Glu Asn Glu Lys
            195                 200                 205

Leu Lys Lys Phe Phe Asn Ile Leu Thr Val Asn Thr Asp Gly Lys Thr
210                 215                 220

Glu Phe Ile Ser Ser Met Glu Gly Tyr Lys Tyr Pro Ile Tyr Ala Val
225                 230                 235                 240

Gln Trp His Pro Glu Lys Ala Pro Phe Glu Trp Lys Lys Leu Arg Gly
                245                 250                 255

Ile Ser His Ala Pro Asn Ala Val Lys Thr Ser Phe Tyr Leu Ala Lys
            260                 265                 270

Phe Phe Ile Ser Glu Ala Leu Lys Asn Asp His His Phe Glu Asn Glu
            275                 280                 285

Leu Glu Glu Thr Glu Ser Leu Ile Tyr Gln Phe Cys Pro Val Tyr Thr
290                 295                 300

Gly Asn Ile Ser Ser Phe Gln Gln Ala Tyr Met Phe Asn
305                 310                 315
```

(2) INFORMATION FOR SEQ ID NO:13:

(i) SEQUENCE CHARACTERISTICS:
(A) LENGTH: 72 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:13:

```
ATGGCCAGTC CGGGCTGCCT GCTGTGCGTG CTGGGCCTGC TACTCTGCGG GGCGGCGAGC    60

CTCGAGCTGT CT                                                        72
```

(2) INFORMATION FOR SEQ ID NO:14:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:14:

```
Met Ala Ser Pro Gly Cys Leu Leu Cys Val Leu Gly Leu Leu Leu Cys
1               5                   10                  15

Gly Ala Ala Ser Leu Glu Leu Ser
            20
```

(2) INFORMATION FOR SEQ ID NO:15:

(i) SEQUENCE CHARACTERISTICS:
        (A) LENGTH: 1280 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
TGCCGCAGCC CCCGCCCGCC CGCAGAGCTT TGAAAGGCG GCGGGAGGCG GCGAGCGCCA    60

TGGCCAGTCC GGGCTGCCTG CTGTGCGTGC TGGGCCTGCT ACTCTGCGGG GCGGCGAGCC   120

TCGAGCTGTC TAGACCCCAC GGCGACACCG CCAAGAAGCC CATCATCGGA ATATTAATGC   180

AAAAATGCCG TAATAAAGTC ATGAAAAACT ATGGAAGATA CTATATTGCT GCGTCCTATG   240

TAAAGTACTT GGAGTCTGCA GGTGCGAGAG TTGTACCAGT AAGGCTGGAT CTTACAGAGA   300

AAGACTATGA ATACTTTTC AAATCTATTA ATGGAATCCT TTTCCCTGGA GGAAGTGTTG    360

ACCTCAGACG CTCAGATTAT GCTAAAGTGG CCAAAATATT TTATAACTTG TCCATACAGA   420

GTTTTGATGA TGGAGACTAT TTTCCTGTGT GGGGCACATG CCTTGGATTT GAAGAGCTTT   480

CACTGCTGAT TAGTGGAGAG TGCTTATTAA CTGCCACAGA TACTGTTGAC GTGGCAATGC   540

CGCTGAACTT CACTGGAGGT CAATTGCACA GCAGAATGTT CCAGAATTTT CCTACTGAGT   600

TGTTGCTGTC ATTAGCAGTA GAACCTCTGA CTGCCAATTT CCATAAGTGG AGCCTCTCCG   660

TGAAGAATTT TACAATGAAT GAAAAGTTAA AGAAGTTTTT CAATGTCTTA ACTACAAATA   720

CAGATGGCAA GATTGAGTTT ATTTCAACAA TGGAAGGATA TAAGTATCCA GTATATGGTG   780

TCCAGTGGCA TCCAGAGAAA GCACCTTATG AGTGGAAGAA TTTGGATGGC ATTTCCCATG   840

CACCTAATGC TGTGAACCCC GCATTTTATT TAGCAGAGTT TTTTGTTAAT GAAGCTCGGA   900

AAAGAACCA TCATTTTAAA TCTGAATCTG AAGAGGAGAA AGCATTGATT TATCAGTTCA    960

GTCCAATTTA TACTGGAAAT ATTTCTTCAT TTCAGCAATG TTACATATTT GATTGAAAGT   1020

CTTCAATTTG TTAACAGAGC AAATTTGAAT AATTCCATGA TTAAGCTGTT AGAATAACTT   1080

GCTACTCATG GCAAGATTAG GAAGTCACAG ATTCTTTTCT ATAATGTGCC TGGCTCTGAT   1140

TCTTCATTAT GTATGTGACT ATTTATATAA CATTAGATAA TTAAATAGTG AGACATAAAT   1200

AGAGTGCTTT TTCATGGAAA AGCCTTCTTA TATCTGAAGA TTGAAAAATA AATTTACTGA   1260

AATACAAAAA AAAAAAAAA                                               1280
```

(2) INFORMATION FOR SEQ ID NO:16:

(i) SEQUENCE CHARACTERISTICS:
        (A) LENGTH: 318 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:16:

```
Met Ala Ser Pro Gly Cys Leu Leu Cys Val Leu Gly Leu Leu Cys
  1               5                  10                  15

Gly Ala Ala Ser Leu Glu Leu Ser Arg Pro His Gly Asp Thr Ala Lys
                 20                  25                  30

Lys Pro Ile Ile Gly Ile Leu Met Gln Lys Cys Arg Asn Lys Val Met
                 35                  40                  45

Lys Asn Tyr Gly Arg Tyr Tyr Ile Ala Ala Ser Tyr Val Lys Tyr Leu
     50                  55                  60

Glu Ser Ala Gly Ala Arg Val Val Pro Val Arg Leu Asp Leu Thr Glu
 65                  70                  75                  80

Lys Asp Tyr Glu Ile Leu Phe Lys Ser Ile Asn Gly Ile Leu Phe Pro
                 85                  90                  95

Gly Gly Ser Val Asp Leu Arg Arg Ser Asp Tyr Ala Lys Val Ala Lys
                100                 105                 110

Ile Phe Tyr Asn Leu Ser Ile Gln Ser Phe Asp Asp Gly Asp Tyr Phe
                115                 120                 125

Pro Val Trp Gly Thr Cys Leu Gly Phe Glu Glu Leu Ser Leu Leu Ile
                130                 135                 140

Ser Gly Glu Cys Leu Leu Thr Ala Thr Asp Thr Val Asp Val Ala Met
145                 150                 155                 160

Pro Leu Asn Phe Thr Gly Gly Gln Leu His Ser Arg Met Phe Gln Asn
                165                 170                 175

Phe Pro Thr Glu Leu Leu Leu Ser Leu Ala Val Glu Pro Leu Thr Ala
                180                 185                 190

Asn Phe His Lys Trp Ser Leu Ser Val Lys Asn Phe Thr Met Asn Glu
                195                 200                 205

Lys Leu Lys Lys Phe Phe Asn Val Leu Thr Thr Asn Thr Asp Gly Lys
                210                 215                 220

Ile Glu Phe Ile Ser Thr Met Glu Gly Tyr Lys Tyr Pro Val Tyr Gly
225                 230                 235                 240

Val Gln Trp His Pro Glu Lys Ala Pro Tyr Glu Trp Lys Asn Leu Asp
                245                 250                 255

Gly Ile Ser His Ala Pro Asn Ala Val Asn Pro Ala Phe Tyr Leu Ala
                260                 265                 270

Glu Phe Phe Val Asn Glu Ala Arg Lys Lys Asn His His Phe Lys Ser
                275                 280                 285

Glu Ser Glu Glu Glu Lys Ala Leu Ile Tyr Gln Phe Ser Pro Ile Tyr
                290                 295                 300

Thr Gly Asn Ile Ser Ser Phe Gln Gln Cys Tyr Ile Phe Asp
305                 310                 315
```